United States Patent
Harrod et al.

(10) Patent No.: US 6,319,432 B1
(45) Date of Patent: Nov. 20, 2001

(54) BISPHENOL-A BIS(DIPHENYL PHOSPHATE)-BASED FLAME RETARDANT

(75) Inventors: William B. Harrod, Minden; W. Dirk Klobucar, Baton Rouge, both of LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/330,688

(22) Filed: Jun. 11, 1999

(51) Int. Cl.[7] .............................. C09K 21/12; C07F 9/12; C07F 9/02; C08K 5/52
(52) U.S. Cl. .......................... 252/609; 558/162; 558/92; 558/110; 524/127; 524/145; 524/141; 524/143
(58) Field of Search .......................... 558/162, 92, 110; 524/127, 145, 141, 143; 252/609

(56) References Cited

U.S. PATENT DOCUMENTS

| | | | |
|---|---|---|---|
| Re. 36,188 | 4/1999 | Gosens et al. | 524/125 |
| 2,520,090 | 8/1950 | Barrett | 260/461 |
| 3,174,931 | 3/1965 | Matson et al. | 252/37.2 |
| 3,254,973 | 6/1966 | Giammaria et al. | 44/69 |
| 3,317,636 | 5/1967 | Lovell et al. | 558/162 |
| 3,360,591 | 12/1967 | Giammaria et al. | 558/162 |
| 4,107,232 | 8/1978 | Haaf et al. | 260/876 R |
| 4,223,100 | 9/1980 | Reinert | 525/146 |
| 4,463,130 | 7/1984 | Serini et al. | 525/67 |
| 4,692,488 | 9/1987 | Kress et al. | 524/139 |
| 4,837,276 | 6/1989 | Fuhr et al. | 524/125 |
| 4,966,814 | 10/1990 | Ohzeki | 428/457 |
| 5,061,745 | 10/1991 | Wittmann et al. | 524/139 |
| 5,204,394 | 4/1993 | Gosens et al. | 524/125 |
| 5,278,212 | 1/1994 | Nishihara et al. | 524/141 |
| 5,281,741 | 1/1994 | Gunkel et al. | 558/92 |
| 5,391,690 | 2/1995 | Kanno et al. | 528/198 |
| 5,420,327 | 5/1995 | Bright et al. | 558/99 |
| 5,455,292 | 10/1995 | Kakegawa et al. | 524/141 |
| 5,672,645 | 9/1997 | Eckel et al. | 524/127 |
| 5,750,756 | 5/1998 | Bright et al. | 558/162 |
| 5,756,798 | 5/1998 | Stults | 558/99 |
| 5,952,408 | 9/1999 | Lee et al. | 524/127 |

FOREIGN PATENT DOCUMENTS

| | | |
|---|---|---|
| 0 074 112 A1 | 3/1983 | (EP) . |
| 0 103 230 A3 | 3/1984 | (EP) . |
| 0 074 112 B2 | 6/1993 | (EP) . |
| 0 767 204 A2 | 4/1997 | (EP) . |
| 0 936 243 A2 | 8/1999 | (EP) . |
| 734767 | 8/1955 | (GB) . |
| 2 043 083 A | 10/1980 | (GB) . |
| 50-51154 | 5/1975 | (JP) . |
| 59-24736 | 2/1984 | (JP) . |
| 59-45351 | 3/1984 | (JP) . |
| 59-202240 | 11/1984 | (JP) . |
| 63-117057 | 5/1988 | (JP) . |
| 5-186681 | 7/1993 | (JP) . |
| 10-25298 | 1/1998 | (JP) . |
| WO 97/47631 | 12/1997 | (WO) . |
| WO 98/35970 | 8/1998 | (WO) . |
| WO 99/11713 | 3/1999 | (WO) . |
| WO 99/55771 | 11/1999 | (WO) . |

OTHER PUBLICATIONS

Burckhardt Helferich and Karl Gunther Schmidt, "Esters and Polyesters of Phosphoric Acids and Cycloalkylphosphonic Acids with Phenols," Chemical Institute, Bonn University, Chem. Ber. 92, pp 2051–2056 (w/translation), (1959).

*Primary Examiner*—Joseph D. Anthony
(74) *Attorney, Agent, or Firm*—E. E. Spielman, Jr.

(57) ABSTRACT

Disclosed is a flame retardant comprising bisphenol A bis(diphenyl phosphate) and its dimer, the former having an HPLC determined 78 to 87 area % and an 85 to less than 90 normalized area %, the normalized area % being based on the total HPLC area % of the bisphenol A bis(diphenyl phosphate) and the dimer. The flame retardant also has a low isopropenylphenyl diphenyl phosphate and a low triphenylphosphate content.

5 Claims, No Drawings

BISPHENOL-A BIS(DIPHENYL PHOSPHATE)-BASED FLAME RETARDANT

BACKGROUND OF THE INVENTION

This invention relates to a novel liquid flame retardant having a high bisphenol-A bis(diphenyl phosphate) content.

Bisphenol-A bis(diphenyl phosphate) is a well known flame retardant for use in normally flammable resins and is especially useful in flame retarding polycarbonate/acrylonitrile-butadiene-styrene (PC/ABS) compositions. It also finds use as a flame retardant in polyphenylene oxide/styrene compositions.

The art is replete with processes and process improvements for the production of bisphenol-A bis(diphenyl phosphate). See, for example, U.S. Pat. No. 2,520,090; U.S. Pat. No. 5,281,741; U.S. Pat. No. 5,750,756; GB 734,767; and WO 98/35970.

Despite past efforts, there is still a need for a liquid bisphenol-A bis(diphenyl phosphate)-based flame retardant which is resistant to crystallization at room temperature but which has a high phosphate content and a very low impurity content. It is an object of this invention to address such need. It is also an object of this invention to provide an improved bisphenol-A bis(diphenyl phosphate)-based flame retardant. It is a further object of this invention to provide a resin formulation containing the bisphenol-A bis(diphenyl diphosphate)s of the invention.

THE INVENTION

In its broadest sense, this invention provides a bisphenol-A bis(diphenyl phosphate) monomer-based flame retardant which is a liquid at room temperature, i.e., 20 to 25° C., and which is resistant to the fonnation of crystals over time. In a preferred form, this invention provides a flame retardant comprising bisphenol-A bis(diphenyl phosphate) and its dimer, the former having from about 78 to about 87 HPLC area % and from about 85 to less than 90 normalized area %, the normalized area % being based on the total HPLC area % of the bisphenol-A bis(diphenyl phosphate) and the dimer.

Additionally, this invention provides a bisphenol-A bis(diphenyl phosphate)-based flame retardant having a low isopropenylphenyl diphenyl phosphate content.

Further, this invention provides a bisphenol-A bis(diphenyl phosphate)-based flame retardant having a low triphenyl phosphate content.

Still further, this invention provides a bisphenol-A bis(diphenyl phosphate)-based flame retardant which is a liquid and is resistant to the formation of crystals and which has a high phosphorus content, a low isopropenylphenyl diphenylphosphate content and a low triphenyl phosphate content.

These and other features of the flame retardants of this invention are more fully discussed below.

DETAILED DESCRIPTION OF THE BIOPHENOL-A BIS(DIPHENYL PHOSPHATE) BASED FLAME RETARDANTS OF THE INVENTION

It has been discovered that it is possible to design a high phosphorus bisphenol-A bis(diphenyl phosphate)-based flame retardant so that, at room temperature, it is a liquid and is resistant to crystallization by specifying that the flame retardant contain certain levels of the dimer of bisphenol-A bis(diphenylphosphate). This discovery is based on work which shows that if the bisphenol-A bis(diphenylphosphate) content of the flame retardant is high, say 90+area % by HLPC, the flame retardant can be a solid at room temperature or if not a solid, a liquid which is very viscous and which has a tendency to form crystals in storage. (Unless otherwise indicated, all area %'s are determined by HPLC.) Thus, it was reasoned that if the bisphenol-A bis(diphenyl phosphate), i.e., the monomer, purity could be reduced by the presence of a specific amount of an impurity, the formation of the solid form or the tendency for crystallization to occur in the liquid form could be avoided. The impurity could not be one which would adversely affect the flame retardant's qualities or its performance in use. In addition, the impurity had to act as a solvent or a melting point depressant for the monomer to hold it in the liquid phase. An ideal impurity, it was discovered, is the dimer of bisphenol-A bis(diphenyl phosphate). The dimer not only attenuates the formation of a solid flame retardant or crystallization in the liquid form, it is also a contributor to the total phosphorus content of the flame retardant. (It is pointed out that the trimer of bisphenol-A bis(diphenyl phosphate) is also an impurity which contributes to the same functions as the dimer. However, the amount of trimer present is usually quite small and thus, focus is kept on the dimer in defining the flame retardants of this invention.) The dimer is easily obtained in situ as it is a product of the process for producing the bisphenol-A bis(diphenyl phosphate) from the reaction of $POCl_3$ and bisphenol-A followed by the reaction of phenol with the first reaction product. Not any amount of dimer, however, is suitable for these purposes.

The amount of dimer needed is tied to the amount of bisphenol-A bis(diphenyl phosphate) in the flame retardant. For the flame retardants of this invention, the amount of bisphenol-A bis(diphenyl phosphate) lies within the range of from about 78 to 87 area %, preferably 80 to 85 area %, amd most preferably 82 to 85 area %. The amount of dimer needed is that amount which will give a normalized area % for the bisphenol-A bis(diphenyl phosphate) which is within the range of from about 83 to less than about 90%, preferably from about 85 to about 89%, and most preferably from about 85 to about 88%. Again, the normalized area % is based on the total of the area %'s for the bisphenol-A bis(diphenyl phosphate) and its dimer. If less dimer than recited above is used, its useful effects are diminished, if more dimer is used, then the character of the flame retardant and its use in a resin formulation is affected. For each bisphenol-A molecule used to produce bisphenol-A bis(diphenyl phosphate), there are two phosphorus substituents, whereas for each molecule of bisphenol-A used to produce the dimer, there are only one and one-half phosphorus substituents. The structural formulas of the two make that clear. The bisphenol-A bis(diplhenyl phosphate) molecule, which can be referred to as a monomer, has the structure:

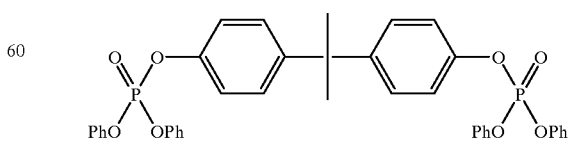

which has two phosphorus substituents per bisphenol-A constituent.

The dimer has the structure:

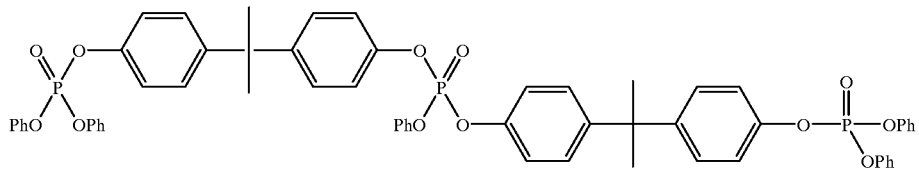

which has three phosphorus substituents for the two bisphenol-A constituents.

The amount of dimer in the flame retardants of this invention is within the range of from about 10 to about 13 area %, preferably from about 11 to about 13 area %, and most preferably from about 12 to about 13 area %.

The flame retardants of this invention will also have a trimer content, the trimer having the structure:

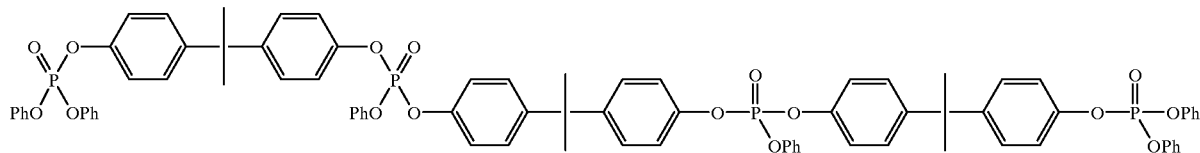

The role that the dimer content (or the trimer content) plays in determining that a bisphenol-A bis(diphenyl phosphate)-based flame retardant is liquid at room temperature and is resistant to crystallization during storage is not reported in the prior art. In addition, there is no known prior art method for specifically obtaining the required dimer contents of this invention. The method for producing the flame retardants of this invention is disclosed below.

The flame retardants of this invention also feature a very low isopropenylphenyl diphenyl phosphate content. This compound is considered by some in the resin formulation industry as a deleterious impurity whose presence must be minimized. The flame retardants of this invention preferably contain no more than 0.01 area % of this impurity. The structure for this impurity is:

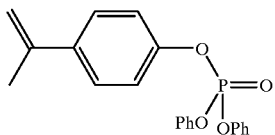

It has been found that the isopropenylphenyl diphenyl phosphate content is not reduced by simply washing the crude product precursor to the final flame retardants of this invention. It is believed that the content of this impurity in the final flame retardant is determined early on in the manufacturing sequence. More discussion on this aspect is found below.

A widely recognized and particularly troublesome impurity found in bisphenol-A bis(diphenyl phosphate)-based flame retardants is triphenylphosphate. This impurity tends to "juice" in the resin formulation and adversely affect the formulation's physical characteristics. The flame retardants of this invention are advantaged as they contain less than about 2.5 area % triphenyl-phosphate and preferably less than about 2.0 area %. Most preferred are flame retardants containing less than about 1.5 area % of this impurity.

The flame retardants of this invention, after washing and neutralization, will have an acid number less than about 2.0 mg KOH/g and preferably less than about 0.15 mg KOH/g.

The melting point range of the flame retardants of this invention is found to be below room temperature, say 20–25° C.

The flame retardants of this invention are best described as viscous oils at room temperature. Their viscosity is within the range of from about 16,000 to 18,500 cP at 25° C., about 2200 to 2400 cP at 40° C. and about 40–60 cP at 100° C.

PROCESSES FOR THE MANUFACTURE OF THE BISPHENOL-A BIS(DIPHENYL PHOSPHATE) BASED FLAME RETARDANTS OF THIS INVENTION.

The flame retardants of this invention are produced in a two step process. The first step entails producing the intermediate, diphosphorotetrachloridate of bisphenol-A, and, to a specified extent, its dimer (and trimer), by gradually adding, over time, bisphenol-A to a reactor containing an excess of phosphorus oxyhalide, the halide being bromine or chlorine, and a catalytic amount of a metal halide, e.g., magnesium chloride.

Experimental work has shown that the obtainment of the desired monomer to dimer relationship is dependent upon the mole ratio of $POCl_3$ to bisphenol-A in the first step of the process and the selected process catalyst. Further work has also suggested that vigorous agitation and the rate of bisphenol-A addition can increase the amount of monomer produced.

It is preferred that the ratio of $POCl_3$ to bisphenol-A be within the range of from about 3.5:1 to about 4.5:1. These ratios define a large excess of $POCl_3$ above the stoichiometric amounts. Such excesses serve an additional purpose, that is, the excess $POCl_3$ acts as a solvent for the process. Thus, no other process solvents, organic or otherwise, are needed.

The preferred catalyst is $MgCl_2$ for use in both process steps. The amount of catalyst used in the first step is generally in an amount of from about 0.01 to about 4.0 wt % based on the weight of the bisphenol-A fed. In the second step, if the catalyst is the same as that used in the first step, the original catalyst provided remains in the reaction mass and is sufficient for the second step. If the second step catalyst is different than the first step catalyst, then there is provided about 0.8 wt % catalyst, based on the weight of the bisphenol-A fed to the reaction mass. Other suitable catalyst include, metal halide salts such as aluminum chloride, calcium chloride, zinc chloride and titanium tetrachloride.

It is preferred that the bisphenol-A be added to the $POCl_3$ in increments or on a continuous basis. As mentioned previously, experimental work has suggested that the monomer/dimer relationship, i.e., the normalized area % of the bisphenol-A bis(diphenyl phosphate), can be affected by adjusting the rate of feed of the bisphenol-A to the $POCl_3$. The trend suggests that high rates of bisphenol-A addition favor the production of the monomer. It is believed that for a particular set of process parameters and for a particular reactor size and configuration, the determination of the best bisphenol-A feed rates is performed by trial and error.

During and after the bisphenol-A addition, HCl is removed from the reaction mass as it evolves therefrom.

The reaction mass temperature during the bisphenol-A addition is kept within the range of from about 85 to about 106° C. to insure that the reaction between the $POCl_3$ and bisphenol-A proceeds expeditiously. After the bisphenol-A addition is complete, the reaction mass is maintained until the reaction is deemed complete. The bisphenol-A feed and temperature maintenance periods together can range from 3 to 6 hours, and more usually from 4 to 5 hours. If the temperature is too low during the bisphenol-A addition and temperature maintenance periods, say below 70° C., it is believed that the final bisphenol-A bis(diphenyl phosphate)-based product will contain a high amount of isopropenylphenyl diphenylphosphate. It is theorized that a low temperature slows the reaction between the $POCl_3$ and bisphenol-A thereby giving more opportunity for a breakdown of the bisphenol-A reactant to phenol and isopropenylphenol, which in turn react with $POCl_3$ to yield isopropenylphenyl diphenyl phosphate.

After all or essentially all of the bisphenol-A has been reacted with the $POCl_3$, which can be monitored by noting HCl evolution, the reaction mass is heated under a reduced pressure to distill off the excess $POCl_3$. Pressures of about 50 torr can be used. Distillation pot temperatures beginning at 50° C. and ending at 150 to 160° C. are suitable. Alternatively, the $POCl_3$ can be removed by stripping the heated reaction mass with an inert gas such as nitrogen. The distillation continues until typically <3.5 mole % phosphorus as $POCl_3$ is detected in the reaction mass by $^{31}$P-NMR. It is important to reduce the amount of $POCl_3$ in the reaction mass to a minimum because the remaining $POCl_3$ will react with the phenol added in the second step to produce the undesired impurity, triphenyl phosphate. The lower the $POCl_3$ remaining in the reaction mass going to the second step, the lower the triphenyl phosphate concentration.

In the second step, the resultant intermediate product (monomer, dimer and trimer) from the $POCl_3$ distillation is reacted with phenol in the presence of any one of the previously discussed catalysts. The phenol, in the molten state, is fed to the intermediate reaction mass which is at a temperature of from about 130 to about 160° C. The amount of phenol fed provides from about 3.8 to about 4, and preferably about 3.9 moles of phenol per mole of bisphenol-A fed in the first step. The reaction mass is kept at a temperature of from about 130 to about 180° C. until no further evolution of HCl is detected. In some cases, it may be advantageous to add a small amount of phenol after the last HCl is detected to insure that the reaction is indeed complete. If indicated by NMR or if no evolved HCl is detected after this addition, then the reaction is confirmed as being complete. Generally, the reaction time (at the above temperatures) for the second step is within 24 hours and preferably occurs in about 6 hours which includes addition times of less than three hours.

After the reaction has been deemed complete, the reaction mass is dissolved in an organic solvent and washed with caustic, which can be sodium or potassium hydroxide. Multiple water washes are also used. After each washing, there is a phase separation. After the washing, the organic solvent is removed by heating under a reduced pressure. Typical organic solvents are methyl-cyclohexane, toluene, xylene, cyclohexane, heptane, and mixtures of any two or more of the foregoing. Most preferred is a 50 wt % mix of methylcyclohexane and toluene.

EXAMPLES ILLUSTRATING THE FEATURES OF THE INVENTION

The following Examples illustrate the principles of the invention. Examples I and IV–XI are of the invention. Examples II and III are comparative experiments and are not of the present invention. The abbreviations used are: DPP= diphenyl phosphate; TPP=triphenyl phosphate; IPP= isopropenyl phenyl diphenylphosphate; and BPADP= bisphenol-A bis(diphenyl phosphate). The BPDAP normalized area % was calculated in accordance with, $$\text{BPDAP Normalized Area \%} = \frac{\text{BPDAP area \%}}{\text{BPDAP area \% + dimer area \%}}$$

EXAMPLE I

Step1

A 4 necked 2000 ml round-bottom flask was equipped with a mechanical stirrer, a Friedrich condenser stacked on top of an Allihn condenser (tap water used for coolant), and a thermocouple well. The glassware was dried and flushed with nitrogen. A nitrogen blanket was maintained on the contents of the flask by having a nitrogen flow (0.5–1.0 SCFH) T'eed into a line connecting the condenser and a scrubber solution (water or caustic will work) to absorb the HCl that is evolved. The flask containing the scrubber solution was placed on a balance to determine the mass of the HCl evolved. To the pot was added $POCl_3$ (1226 g, 7.99 mol) and anhydrous magnesium chloride (3.56 g, 37.4 mmol). The reaction mixture was warmed to 98° C. and the BPA (456 g, 2.00 mol) was added portion-wise as shown in the Table below.

TABLE I

| Time (hr) | Temp. (° C.) | HCl Trap Wt. Gain (g) | BPA Added (g) |
| --- | --- | --- | --- |
| 0.00 | 98 | 0 | 31.1 |
| 0.25 | 99 | 6.2 | 29.3 |
| 0.58 | 99 | 16.0 | 31.0 |
| 0.078 | 97 | 25.7 | 36.1 |
| 1.00 | 99 | 38.9 | 33.7 |
| 1.08 | 95 | 48.3 | 0 |
| 1.18 | 100 | 50.3 | 0 |
| 1.25 | 100 | 51.2 | 30.9 |
| 1.50 | 101 | 60.8 | 30.8 |
| 1.60 | 967 | 70.0 | 0 |
| 1.75 | 101 | 71.6 | 35.1 |
| 2.00 | 101 | 83.7 | 30.3 |
| 2.25 | 101 | 94.0 | 37.2 |
| 2.37 | 97 | 105 | 0 |
| 2.50 | 101 | 106.6 | 31.5 |
| 2.75 | 101 | 117.5 | 31.5 |

TABLE I-continued

| Time (hr) | Temp. (° C.) | HCl Trap Wt. Gain (g) | BPA Added (g) |
|---|---|---|---|
| 3.00 | 101 | 127.9 | 34.6 |
| 3.08 | 98 | 136.4 | 0 |
| 3.25 | 101 | 139.8 | 31.7 all BPA in now |
| 3.42 | 100 | 149.4 | 0 |
| 3.52 | 101 | 150.1 | Temp reset to 110° C. |
| 3.80 | 108 | 151.6 | |
| 4.00 | 112 | 152.4 | |
| 4.25 | 109 | 152.2 | Heat off, cooling |

A sample of the reaction mixture was looked at by $^1$H NMR (CDCl$_3$) and it showed that all of the BPA had reacted.

The condenser stack was replaced with a 1 piece distillation takeoff/condenser. The mechanical stirrer was replaced with a magnetic stirrer and the condenser was cooled with antifreeze at −15° C. The excess POCl$_3$ was removed by vacuum distillation at 33–61° C./50 torr at a pot temperature of 53–156° C. The distillation was ended when there was about 30 seconds between distillate drops. There was obtained 584 g of clear, colorless recovered POCl$_3$. A $^{31}$P NMR (CDCl$_3$) showed that the distillation pot residue contained about 0.8 mol % of POCl$_3$.

Step 2

The magnetic stirrer was replaced with a mechanical stirrer and the stack of condensers returned in place of the distillation takeoff/condenser. A 250 ml jacketed addition funnel on an offset adapter was mounted on the 2000 ml flask. A nitrogen blanket was maintained on the contents of the flask by having a nitrogen flow (0.2–1.0 SCFH) T'eed into a line connecting the condenser and a scrubber solution (water or caustic will work) to absorb the HCl that is evolved. The flask containing the scrubber solution was placed on a balance to determine the mass of the HCl evolved. The reaction mixture was stirred while it was warmed to about 145° C. and the molten phenol (752 g, 7.99 mol) was added as shown in the table below.

TABLE II

| Time (hr) | Temp. (° C.) | Phenol (ml, TD) | HCl Trap Wt. Gain (g) |
|---|---|---|---|
| 0.00 | 153 | 260 (269.6 g) | 0.0 |
| 0.15 | 159 | 250 | 1.6 |
| 0.40 | 153 | 220 | 15.6 |
| 0.67 | 154 | 150 | 43.4 |
| 0.92 | 156 | 105 | 61.7 |
| 1.17 | 156 | 70 | 76.3 |
| 1.42 | 156 | 35 | 90.5 |
| 1.67 | 157 | 0 | 105.4 |
| 1.73 | 157 | 270 (270 g) | 107.1 |
| 2.17 | 158 | 200 | 131.0 |
| 2.42 | 158 | 187 | 136.4 |
| 2.67 | 156 | 80 | 165.6 |
| 2.40 | 159 | <25 | 198.3 |
| 2.93 | 159 | 205 (212.5 g) | 201.3 |
| 3.33 | 160 | 87 | 243.0 |
| 3.67 | 158 | <25 | 260.0 |
| 3.95 | 160 | 0 (all phenol added) | 272.1 |
| 4.15 | 160 | 0 | 276.9 |
| 4.47 | 160 | 0 | 280.1 |
| 4.65 | 160 | 0 | 280.9 |
| 4.93 | 160 | 0 | 281.5 |
| 5.20 | 160 | 0 | 281.7 |
| 5.43 | 160 | 0 | 281.7 (heat off. cooling down) |

The reaction mixture (1362 g) was transferred to a jacketed wash kettle (5 liter 4 necked flask with a botiom drain and a mechanical stirrer) with a mixture of 1000 g of toluene and 1004 g of methylcyclohexane. The reaction mixture was washed at 60–72° C. with 300 g of 10 wt % aqueous potassium hydroxide (all of the other experiments used 10 wt % aq. sodium hydroxide, obtained 434 g of aqueous phase, pH~14), 300 g of 5 wt % aqueous potassium hydroxide (obtained 334 g of aqueous phase, pH~14), 301 g of tap water (obtained 304 g of aqueous phase, pH~11), 302 g of tap water (obtained 304 g of aqueous phase, pH~8), and then 302 g of tap water (obtained 307 g of aqueous phase, pH~7). There was obtained 3157 g of organic phase which was gravity filtered (Whatman $2^V$ paper). The volatiles were removed on a rotavap (2 torr/90° C.). The residual solvent was removed in a vacuum oven at 150° C./2 torr to give 1189 g of slight cloudy colorless product as a viscous oil. The product by HPLC analysis contained 0.07 area % DPP, 0.11 area % phenol, 0.49 area. % half-ester, 0.002 area % IPP, 84.17 area % BPADP, 12.35 area % dimer, and 1.53 area % trimer. 87.2 normalized area % for the BPADP was caculated.

EXAMPLES II and III (Comparative Examples)

Example II was run in a manner similar to Example I except that it was run in ¼ scale and used laboratory glassware. Example III was run in the manner of Example I. The process parameters of Examples I and II are recited in Table III.

EXAMPLES IV–IX (Of the Invention)

Examples IV–IX were run in the manner of Example I. The process parameters of Examples IV–IX are recited in Table III.

TABLE III

| | Ex. II | Ex. III | Ex. IV | Ex. V | Ex. VI | Ex. VII | Ex. VIII | Ex. IX |
|---|---|---|---|---|---|---|---|---|
| Reaction Step 1 | | | | | | | | |
| POCl3 (g) | 230 | 920 | 1077 | 1150 | 1153 | 1226 | 1227 | 1227 |
| BPA (g) | 113 | 451 | 457 | 457 | 457 | 458 | 457 | 457 |
| MgCl2 (g) | 0.851 | 3.49 | 3.58 | 3.5 | 3.51 | 3.56 | 3.52 | 3.5 |
| POCl3:BPA (molar ratio) | 3.0/1 | 3.0/1 | 3.5/1 | 3.75/1 | 3.76/1 | 4.0/1 | 4/1 | 4.0/1 |
| Total HCl (g) evolved | 44.4 | 149 | 154.3 | 155 | 155 | 152 | 153 | 144 |
| BPA total feed time (hr) | 2.5 | 3.5 | 3.3 | 2 | 2 | 3.25 | 2 | 1.25 |

TABLE III-continued

| | Ex. II | Ex. III | Ex. IV | Ex. V | Ex. VI | Ex. VII | Ex. VIII | Ex. IX |
|---|---|---|---|---|---|---|---|---|
| BPA feed rate (g/min) | 20/30 | 30/15 | 31/15 | 30/8 | 30/8 | 30/15 | 30/8 | 30/5 |
| Total Reaction Time (hr) | 5 | 4.4 | 4.3 | 2.75 | 2.6 | 4.25 | 2.75 | 1.8 |
| Reaction Temperature (° C.) | 88–109 | 95–110 | 97–110 | 91–112 | 92–112 | 95–12 | 90–112 | 94–114 |
| POC13 Strip | | | | | | | | |
| Final Pot Temp (° C.)/mm Hg | 141/60 | 153/50 | 155/50 | 154/50 | 145/50 | 154/50 | 145/50 | 145/50 |
| Total Strip time (hr) | 1 | 1.2 | 1.9 | 1.7 | 1.2 | 1.3 | 0.8 | 0.9 |
| Dry Xylene Chaser added [(g) or No] | No | No | No | No | No | No | No | No |
| Distillate Obtained (g) | 65.9 | 270 | 294 | 513 | 507 | 584 | 566 | 600 |
| POC13 Remaining by P31 NMR (mol %) | 1.2 | 3.2 | 0.7 | 0.3 | 1.6 | 0.8 | 1.9 | 1.2 |
| Reaction Step 2 | | | | | | | | |
| MgCl2 (g) | 0 | 0 | 0 | 0 | 0 | 0 | 0 | 0 |
| Phenol (g) | 189 | 740 | 742 | 741 | 743 | 752 | 742 | 747 |
| Addition Time (hr) | 1.25 | 4.2 | 2.3 | 1.6 | 1.5 | 4 | 1.5 | 1.5 |
| Addition Temp (° C.) | 154–162 | 155–160 | 151–158 | 152–157 | 143–145 | 153–160 | 143–147 | 137–151 |
| Final Reaction Temp (° C.) | 170 | 170 | 160 | 157–159 | 159 | 160 | 158–159 | 143–166 |
| Final Cook Time (hr) | 1 | 2.3 | 1.7 | 1.7 | 1.5 | 1.5 | 2.6 | 2.4 |
| Total HCl Evolved (g) | 62 | 285 | 271 | 270 | 276.2 | 282 | 252+ | 273.1 |
| Work-Up | | | | | | | | |
| Wt. Crude Product before washes (g) | — | 1351 | 1343 | 1361 | 1362 | 1362 | — | 1372 |
| Toluene Added (g) | 255 | 1001 | 1025 | — | 1001 | 1000 | — | — |
| Methylcyclohexane Added (g) | 250 | 972 | 1000 | — | 1002 | 1004 | | |
| Recovered MCH/Toluene used (g) | — | — | — | 2000 | 0 | — | 1999 | 2016 |
| Wash and Phase Cut Temp (° C.) | 66 | 71 | 70 | 70 | 70 | 70 | 68 | 68 |
| 1st Caustic Wash (g/wt %) | 150/10 | 306/10 | 307/10 | 201/10 | 305/10 | 300/10 | 300/5 | 109/10 |
| Aqueous Removed (g) | 191 | 364 | 462 | 447 | 429 | 434 | 359 | 357 |
| 2nd Caustic Wash (g/wt %) | 152/10 | 301/10 | 306/10 | 304/10 | 301/10 | 300/5 | 302/10 | 308/10 |
| Aqueous Removed (g) | 160 | 310 | 333 | 341 | 338 | 334 | 365 | 316 |
| 1st Water Wash (g) (* = tap water) | 153* | 305* | 302* | 307* | 302* | 302* | 304* | 305* |
| Aqueous Removed (g/pH) | 151/12 | 306/13 | 299/12 | 315/? | 309/12 | 304/11 | 310/12 | 312/12 |
| 2nd Water Wash (g) | 154* | 305* | 302* | 299* | 303* | 302* | 305* | 306* |
| Aqueous Removed (g/pH) | 160/9 | 304/9 | 303/9 | 297/9 | 301/9 | 304/8 | 303/9 | 305/9 |
| 3rd Water Wash (gm) | 151* | 300* | 300* | 301* | 300* | 302* | 301* | 305* |
| Aqueous Removed (g/pH) | 151/7 | 298 | 296/7 | 301/7 | 297/9 | 307/7 | 305/9 | 306/7 |
| 4th Water Wash (g) | — | — | — | — | 300* | — | 301 | — |
| Aqueous Removed (g/pH) | — | — | — | — | 302/7 | — | 303/7 | — |
| Wt Organic Phase (g) | 771 | 3228 | 3149 | 3107 | 3156 | 3157 | 3190 | 3275 |
| Final Product Weight (g) | 265 | 1241 | 1133 | 1194 | 1197 | 1189 | 1236 | 1281 |
| Yield (%) | 77 | 91 | 82 | 86 | 86 | 86 | 89 | 92 |
| HPLC Results (Area %) | | | | | | | | |
| DPP | 0.26 | 0.11 | 0.11 | 0.12 | 0.1 | 0.07 | 0.11 | 0.09 |
| Phenol | 0.05 | 0.07 | 0.14 | 0.13 | 0.12 | 0.11 | 0.14 | 0.07 |
| TPP | 1.13 | 2.75 | None Det | 0.86 | 1.48 | — | 2.45 | None Det |
| Half Ester | 0.33 | 0.05 | None Det | 0.64 | 0.67 | 0.49 | 0.23 | 1.98 |
| IPP | 0.04 | 0 | None Det | <0.01 | <0.01 | 0 | None Det | 0.05 |
| BPADP (n = 1) | 71 | 76.5 | 81.69 | 83.74 | 83.24 | 84.17 | 84.13 | 84.3 |
| Dimer (n = 2) | 20.52 | 16.62 | 13.95 | 12.64 | 12.55 | 12.35 | 11.22 | 11.57 |
| Trimer (n = 3) | 6.55 | 3.42 | 2 | 1.71 | 1.65 | 1.53 | 1.28 | 1.39 |
| Unknowns | 1.28 | 0.46 | 1.18 | 0.1 | 0.12 | 1.27 | 0.08 | 0.52 |
| Viscosity** | | 115 | 117 | 113 | 110 | 110 | 95.4 | 102 |
| Normalized area % | 77.5 | 82 | 85.4 | 86.8 | 86.8 | 87.2 | 88 | 88 |

** @ 80° C. (cP, ASTM D445)

EXAMPLE X (Of the Invention)

Step 1

Phosphorus oxychloride (POCl$_3$, 306.7 g, 2.0 mol) and MgCl$_2$(0.95 g, 0.01 mol) were added into a 1 L round-bottomed flask equipped with a Friedrich's condenser (8.5° C.). The reaction mass was stirred at 90–95° C. under a pad of nitrogen. BPA was added in six increments 114.9 g (total, 0.50 mol) over 1.5 hours. After an additional 3 hours at 105° C., reaction completion was shown by the weight of HCl evolved into a water scrubber (35.8 g HCl trapped,98% of theoretical). Excess POCl$_3$ was then removed by distillation from the reaction mass until no POCl$_3$ was detected using $^{31}$P-NMR.

Step 2

The reactor was reconfigured with a jacketed addition funnel and nitrogen pad inlet through the addition funnel. The evolved HCl passed through an expansion piece in the reactor neck into an aqueous trap, its weight also used for monitoring the reaction progress. Molten phenol (174.1 g, 1.9 moles at 72° C.) was added dropwise over 1.5 hours into the reactor held at 128–1344° C. and, after addition, reaction proceeded at 148° C. for an additional 3 hours, followed by NMR and HPLC analysis of the crude product. The total mass yield of crude product was 322.1 g (92.3% yield, with BPA as limiting reagent). HPLC showed 69.9% BPADP, 9.07% oligomerics, 11.0% unknowns, 2.3;5% PhOH, no TPP was detected, and the IPP level was <0.01%. An 88.5 normalized area % for BPADP was calculated.

The crude BPADP was purified by dissolving 286.4 g into 483.5 g of mixed solvent (50% wt methylcyclohexane: toluene), then washing with two 150 g portions 10% wt. NaOH. There was a phase separation at 70° C. after each wash. The organic phase was then washed with three portions of water, which was separated from the aqueous phase after each wash. Solvent removal and drying of the organic phase were accomplished by distillation and nitrogen stripping. The organic phase recovery in the purification step was 91.3 wt %. The residual solvent was removed in a vacuum oven (12 hours, 30 mm Hg; 140° C.). The product analysis by HPLC showed 84.7 area % BPADP, 12.0 area % dimer, 1.46 area % trimer, <0.01 area % IPP, 0.11 area % half ester, 0.27 area % DPP.

EXAMPLE XI

(Of the Invention)

The procedure of Example X was followed except that 413.1 g $POCl_3$, 176.6 g of bisphenol-A, 1.51 g $MgCl_2$, and 305.9 g phenol (3.25 moles) were used. The final product contained 80.5 area % bisphenol-A bis(diphenyl phosphate), 11.9 area % dimer, 1.57 area % trimer, <0.01 area % isopiopenyl- phenyldiphenyl phosphate and 1.61 area % triphenyl phosphate.

HPLC Analysis

Method

The HPLC method used to obtain the area % values reported herein is described below. The method uses UV detection at 254 nm with and acetonitrile/water gradient on a reverse phase C18 column.

The sample is dissolved in acetonitrile at a concentration of approximately 2500 ppm. An aliquot of the solution is then transferred to an autosampler vial. A small portion (10 uL) is injected into the HPLC and analyzed under gradient conditions at a wavelength of 254 nm. Area % values are calculated for all peaks in the chromatogram. External standard reference materials are available for the following impurities: DPP, Phenol, BPA, and TPP. Solutions of these reference materials are made up at concentrations of 100 ppm. Each is injected and analyzed following the conditions listed below. Response factors are calculated for each of these reference peaks to allow weight % values for these impurities to be calculated from the sample chromatograms. One impurity, IPP, has been determined to have a UV response significantly greater than the rest of the peaks in the chromatogram. This was determined using other analytical techniques. Since a reference standard is not available for this material, the area value of this peak may be divided by 8 and then area % values for the chromatogram are recalculated.

Details of the instrument, test conditions, peaks and corresponding retention times are listed below.

HPLC Instrumentation

Any suitable HPLC system equipped with a multisolvent delivery system capable of binary gradient elution, UV detection at 254 nm, automatic sample injector capable of 10 $\mu L$ sample injection. The HPLC instrument used to obtain the area % values reported was a Hewlett-Packard Model 1090.

| HPLC Conditions Set the instrument conditions as follows: | |
|---|---|
| Column: | Waters Novapak (4 um) C18 (3.9 × 75 mm) |
| Temperature: | Ambient |
| Flow: | 1.0 mL/minute |
| Detector Wavelength: | 254 nm |
| Injection volume: | 10 $\mu L$ |
| Analysis time: | 30 minutes |

| Gradient Profile: | | |
|---|---|---|
| Time (min) | % Water | % Acetonitrile |
| 0 | 60 | 40 |
| 7 | 5 | 95 |
| 12 | 5 | 95 |
| 18 | 60 | 40 |
| 30 | 60 | 40 |

| Compounds and Approximate Retention Times | |
|---|---|
| DPP | 0.4 min. |
| Phenol | 0.9 min. |
| BPA | 1.9 min. |
| TPP | 5.4 min. |
| Half Ester | 6.2 min. |
| IPP | 7.3 min. |
| BPADP | 8.2 min. |
| n-2 | 10.0 min. |
| n-3 | 12.4 min. |

The flame retardants of this invention can be used in a wide variety of polymer resins. As before noted, they are useful in polycarbonate and acrylonitrile-butadiene-styrene blends (PC/ABS) and in polyphenylene oxide containing blends, especially blends with high impact polystyrene (PPO/HIPS). Other resins in which the flame retardants of this invention are useful are poly-phenylene oxide, high-impact polystyrene, polycarbonate, polyurethane, polyvinyl chloride, acrylonitirle-butadiene-styrene and polybutylene terephthalate. The flame retardants of this invention will generally be use in amounts ranging from 7 to 20 wt % in the resin, based upon the total weight of the entire resin formulation. The flame retardants of this invention are also suitable for use in combination with other formulation constituents. For example, plasticizers, impact modifiers, antioxidants, UV stabilizers, pigments, fillers may be used. Reference to the prior art will identify further constituents which are suitable additives in for resin formulations.

What is claimed is:

1. A flame retardant comprising a predominate amount of bisphenol A bis(diphenyl phosphate), isopropenylphenyl diphenyl phosphate in an amount not to exceed about 0.01 area % and triphenyl phosphate in an amount not to exceed about 2.5 area %, all area %'s being measured by HPLC; said flame retardant being a liquid at room temperature.

2. The flame retardant of claim 1 wherein the triphenyl phosphate is present in a amount not exceeding 1.5 area %.

3. A composition comprising a normally flammable resin and an amount of the flame retardant in claim 1 sufficient to impart flame retardant qualities to the composition.

4. The composition of claim 3 wherein the resin is a thermoplastic resin.

5. The composition of claim 3 wherein the resin is selected from the group consisting of blends of polycarbonate/acrylonitrile-butadiene-styrene and blends of polyphenylene oxide/poly-styrene.

* * * * *